(12) United States Patent  (10) Patent No.: US 8,715,714 B2
Kim et al.  (45) Date of Patent: May 6, 2014

(54) USES OF RARE EARTH ELEMENTS FOR HAIR IMPROVEMENT

(75) Inventors: Sang Hyun Kim, Daegu (KR); Soon Im Choi, Daejeon (KR)

(73) Assignee: Micellbio Co., Ltd. (KR)

( * ) Notice: Subject to any disclaimer, the term of this patent is extended or adjusted under 35 U.S.C. 154(b) by 281 days.

(21) Appl. No.: 12/438,612

(22) PCT Filed: Aug. 24, 2007

(86) PCT No.: PCT/KR2007/004084
§ 371 (c)(1),
(2), (4) Date: Feb. 24, 2009

(87) PCT Pub. No.: WO2008/023960
PCT Pub. Date: Feb. 28, 2008

(65) Prior Publication Data
US 2010/0247428 A1    Sep. 30, 2010

(30) Foreign Application Priority Data

Aug. 25, 2006  (KR) .................. 10-2006-0080931
Feb. 14, 2007  (KR) .................. 10-2007-0015520

(51) Int. Cl.
*A61K 9/00*  (2006.01)
(52) U.S. Cl.
USPC ........................................ 424/429

(58) Field of Classification Search
USPC ................................................ 424/429
See application file for complete search history.

(56) References Cited

U.S. PATENT DOCUMENTS

| 4,551,330 | A  | * | 11/1985 | Wagman et al. | 424/59  |
| 6,150,299 | A  | * | 11/2000 | Umemoto et al. | 502/304 |
| 6,506,413 | B1 | * | 1/2003  | Ramaekers | 424/535 |
| 2005/0118279 | A1 | * | 6/2005 | Blotsky et al. | 424/617 |

FOREIGN PATENT DOCUMENTS

| GB | 1475971 A  | * | 6/1977 |
| JP | 06287111 A1 | * | 1/1994 |

OTHER PUBLICATIONS

Mounsey et al (Am Fam Physician. Aug. 15, 2009;80(4):356-62).*

* cited by examiner

*Primary Examiner* — Benjamin Packard
(74) *Attorney, Agent, or Firm* — Cantor Colburn LLP

(57) ABSTRACT

Disclosed are uses of rare earth element selected from the group consisting of cerium (Ce), praseodymium (Pr), promethium (Pm), europium (Eu), terbium (Tb), dysprosium (Dy), holmium (Ho), erbium (Er), thulium (Tm), ytterbium (Yb), scandium (Sc), yttrium (Y), lanthanum (La), neodymium (Nd), samarium (Sm), gadolinium (Gd), lutetium (Lu) and mixtures thereof, or a salt or an oxide thereof for preventing hair loss, promoting hair regrowth and hair growth, removing and preventing dandruff, or promoting black hair formation.

4 Claims, 10 Drawing Sheets

Composition of Comparative Example

Composition of Example 1

Composition of Example 2

Composition of Comparative Example

Composition of Example 1

Composition of Example 2

USES OF RARE EARTH ELEMENTS FOR HAIR IMPROVEMENT

TECHNICAL FIELD

The present invention relates to uses of rare earth elements for hair improvement, and more specifically, to uses of rare earth elements selected from the group consisting of cerium (Ce), praseodymium (Pr), promethium (Pm), europium (Eu), terbium (Tb), dysprosium (Dy), holmium (Ho), erbium (Er), thulium (Tm), ytterbium (Yb), scandium (Sc), yttrium (Y), lanthanum (La), neodymium (Nd), samarium (Sm), gadolinium (Gd), lutetium (Lu) and mixtures thereof, or a salt or an oxide thereof for preventing hair loss, promoting hair regrowth and hair growth, removing and preventing dandruff, or promoting black hair formation.

BACKGROUND ART

Generally, human body contains about 100,000 to 150,000 hairs. Hairs grow and fall out through the stages of anagen, catagen and telogen with different cycles from one another. This growth cycle repeats with a period of 3 to 6 years, and thus, about 50 to 100 hairs fall out every day. Alopecia refers to a condition which occurs as hairs in anagen are decreased and hairs in catagen and telogen are increased. Alopecia is mainly caused by excessive secretion of androgen, one of male sex hormones, in hair root and sebaceous gland, which intensively stimulates hair follicle cells and contracts hair follicles, thereby to retard hair growth. Other known causes of alopecia include insufficient nutrition due to local blood flow disturbance, excessive secretion of sebum, malfunction of scalp due to peroxides, bacteria, etc., lapse of neurosis due to intensive external stress and chronic diseases, and so on. Interest in hair regeneration is increasing as the generation of alopecia becomes more serious by overwork, environmental pollution, side effects due to misuse and abuse of addictive drugs, scalp blood flow disturbance due to permanent, dyeing, use of mousse, spray, etc., genetic factors and so on. Recently, alopecia in young age is increased including female obese alopecia as well as male pattern alopecia. Therefore, various kinds of hair regrowth or growth agents are commercialized for improving alopecia. Commercially available hair regrowth or growth agents include vasodilators such as capronium chloride, minoxidil, etc., hormone drugs for inhibiting action of male sex hormone such as estrogen, estradiol, etc. and inhibitors of activity of male sex hormone such as pentadecanoic acid, finasteride, etc.

The most commonly used agent for treatment or prevention of alopecia and for promotion of hair regrowth is a minoxidil-containing formulation manufactured by Upjohn Co., Ltd., which is disclosed in U.S. Pat. No. 4,596,812. Minoxidil is one of two hair regrowth ingredients which have been approved by the U.S. Food and Drug Administration (FDA). Minoxidil was originally developed as a drug for treating hypertension for the purpose of reducing blood pressure. However, hair regrowth was observed as a side effect, and thus, this became more famous as a hair regrowth agent. Although a mechanism by which minoxidil acts as a hair regrowth agent has not yet been clearly understood, minoxidil is believed to improve nutrition to hair root by increasing blood flow from vasodilatory action, thereby to promote hair growth. A recent report indirectly supports this increased blood flow model (Br. J. of Dermatol., 1998; 138; 407-411) that minoxidil increases the expression of vascular endothelial growth factor (VEGF), a growth factor associated with vasodilation in dermal papilla, a major cell constituting hair root. In addition to vasodilatory action of minoxidil in hair regrowth, it has been reported that minoxidil promotes activation of dermal papilla cells in hair root cultivated in vitro (Skin Pharmacol., 1996; 9; 3-8) and growth of hair follicles in tissue culture (J. Invest. Dermatol., 1989; 92; 315-320). This suggests that minoxidil may act directly on hair root as a growth factor. Furthermore, finasteride, a main ingredient of Propecia having been recently commercialized by Merck, inhibits conversion of male sex hormone, testosterone, into dihydrotestosterone (DHT), the more potent male hormone than testosterone, by action of 5α-reductase. On December of 1997, 1 mg tablet was approved by FDA as a hair-regrowth agent for treatment of male pattern alopecia, and is now commercially available. In clinical use, it has been proved to have a significant effect (J. Am. Acad. Dermatol., 1998; 39; 578-589). In addition, there have been many efforts to promote hair regrowth by spreading to scalp or orally administering extracts of various natural substances or herbs.

However, minoxidil and capronium chloride, which have been widely used to prevent and treat alopecia, have insufficient clinical effects. Hormone drugs for inhibiting action of male sex hormone or inhibitors of activity of male sex hormone have insufficient clinical effects, or may inhibit male sexual function as a side effect. In addition, they may have a problem in safety in human body since active ingredients thereof are synthetic compounds and they do not show sufficient effect in hair regrowth or hair growth. In case of hair improving compositions containing various natural extracts, their functional mechanism has not been clearly revealed, and their effects have not been sufficiently proved. They also has problems that their active ingredients have low absorbability and poor skin feeling such as stickiness on scalp, and cause skin troubles.

In order to overcome limits of hair regrowth agents due to side effects of chemical drugs, implantation of hairs on scalp has been performed, but it takes much cost and long time to implant hairs one by one. Therefore, implantation is just temporary, but is insufficient as a fundamental treatment.

Hairs consist of three parts: cuticle, cortex and medulla. The cortex surrounding the medulla is the thickest part of hairs (about 80 to 90% of the total thickness of hairs), and includes granules called as melanosome consisting of melanin, lipid membrane, tyrosinase related protein-1 (TRP-1), TRP-2 and other proteins. Melanin is synthesized at melanosome which is an organelle within melanocytes, and is delivered to neighboring keratinocytes through dendrons of melanocytes. In synthetic pathway of melanin, tyrosine, an amino acid, is oxidized to DOPA and the DOPA is further oxidized to dopaquinone, in which step tyrosinase is involved. Subsequent reactions are auto-oxidative, but it is known that enzymes such as TRP-1 and TRP-2 are involved to accelerate the reactions. Brightness of hair is determined by factors such as types and distributed amounts of eumelanin and pheomelanin formed from tyrosine, and thus, each people has unique hair color. Eumelanin is the most common and the darkest pigment, and forms brown or black hair. Pheomelanin has bright color and forms blonde hair. White hair is caused as melanogenesis is stopped at dopaquinone followed by keratinization, and oxidation does not occur since tyrosinase cannot be produced. White hair is more clearly observed in human races having black or brown hairs, and is a kind of aging that occurs as melanogenesis is stopped in melanocytes. In addition to such senile white hair, white hair may further include premature gray hair, hereditary poliosis, acquired poliosis due to vitiligo vulgaris, alopecia areata, etc., white hair due to drugs and chemicals, poliosis due to stress, white hair due to autoimmune diseases, poliosis due to malnutrition and unbalanced nutrition, poliosis due to renal dysfunction, and so on.

Gene therapy may treat hereditary white hair, and Treatment of a disease may treat white hair due to the disease. In other cases, uses of knotgrass, *Sophora flavescens*, sea weed fusiforme, *Rehmannia radix*, *Rehmanniae radix* preparata, mulberry, plantain oil, bamboo oil, bear oil, etc. have been known as folk remedies, but they cannot be expected to have significant effects.

Rare earth elements are trace metal elements, which are contained at about 0.016% in the earth's crust, and refer to minerals including 17 elements, 15 elements of atomic numbers from 57 to 71 (La, Ce, Pr, Nd, Pm, Sm, Eu, Gd, Tb, Dy, Ho, Er, Tm, Yb, Lu) and 2 elements of group 3A (Sc, Y) in the periodic table of elements. Rare earth element may exist in the form of salt in which it is ionically bonded with its counter-ion, for example, in the form of sulfate, nitrate, carbonate, acetate, phosphate, chloride, etc., or in the form of oxide including hydroxide. Rare earth elements are very useful even though they have been found only two hundred years ago, and are not still well-known to public. Since rare earth elements have unique physical and chemical effects due to their unique electronic structures, they have been used in machinery, petrochemistry, photochemistry, etc. as permanent magnet, superconductor or fluorophore, and have been recently tried to be applied in various fields of agriculture, forestry, livestock industry, etc. Furthermore, as biological effects, rare earth elements promote photosynthetic action and chlorophyll production in higher plants; promote shoot formation; increase root vitality; activate respiratory function; promote nutrient transport in plant body; control moisture; promote cell division, hormone transfer, and absorption and transport of nutrients; activates metabolism; increases synthesis of protein and RNA in leaves, etc. In addition, they retard aging of leaves, increase protein contents in green algae, and promote synthesis of protein and chlorophyll by promoting photosynthesis and oxygen releasing activity. $La^{3+}$ is known to increase activity of $(Na^+, K^+)$-ATPase and $Mg^{2+}$-ATPase in cell membrane of human erythrocytes, and thus, strengthen functions of $Ca^{2+}$ ion in human body (The journal of Biological Chemistry, 1986; 261(20); 9552-9557). Some of rare earth elements are known to have antibacterial (Chem. Pharm. Bull, 2003; 51(5); 494-498) and antioxidative activities by preventing generation of reactive oxygen species (Biochemical and Biophysical Research Communication, 2006; 2; 86-91). Further, some of rare earth elements are known to activate cells, promote blood circulation, strengthen metabolism and increase regenerability of tissues by their interaction with far infrared ray as alkaline ions, thereby preventing fatigue and aging. They are also known to increase weight and feed conversion ratio (FCR) in growing fat pigs (J. Anim. Physiol. a. Anim. Nutr., 2001; 85; 263-270). Furthermore, it was found that rare earth elements are low toxic, absorbed by a very small amount through digestive organs, scarcely accumulated in body, and not teratogenic, mutagenic or carcinogenic (Environmental Health Perspectives, 1996; 104; 85-95).

Korean Patent No. 569,083 discloses a UV shielding agent comprising metal oxide doped cerium oxide in which metal ion having larger ion radius than that of $Ce^{4+}$ and/or lower valence metal ion than $Ce^{4+}$ are doped, and a cosmetic composition containing the same. It also describes that the cosmetic composition may be used as a hair cosmetic. However, it relates to the metal oxide doped cerium oxide but does not relate to uses of rare earth elements, or salts or mixtures thereof. U.S. Pat. No. 5,112,360 discloses a hair dye comprising 5,6-dihydroxyindole and/or an indole derivative, and at least one salt of rare earth element. However, it relates to hair dyeing effect of the composition consisting of indole compound and salt of rare earth element, and neither taught nor suggested that rare earth element alone directly promotes the formation of black hairs, when applied to hair or hair root. In addition, Japanese Patent Laid-Open No. 2003-137749 (published on May 14, 2003) discloses a hair concealer charged in a spray container, manufactured by the process in which natural ore containing a radioactive rare earth element such as lanthanum (La), neodymium (Nd), samarium (Sm), gadolinium (Gd) and lutetium (Lu) is pulverized into a particle diameter of ≤5 μm, the pulverized natural ore is mixed with a colorant in a viscous liquid binder composed of an alcoholic solvent and a solute soluble in the solvent to give a mixture, and then, the mixture is charged into a spray container. This Laid-Open Patent relates to a hair concealer with which a hair deficient region is covered so as to be visually hairy, and environments around scalp are improved for regeneration and growth of hairs. It describes that β ray emitted from radioactive rare earth elements attached to scalp after spraying forms anions, thereby promoting blood circulation to promote regeneration and growth of hairs. However, it relates to promotion of blood circulation by β ray emission from natural radioactive rare earth elements, and hair concealing or growth effect derived therefrom, but has no mention on promotion of cell proliferation, inhibition of TGF-β expression, promotion of VEGF expression, promotion of activity and expression of tyrosinase, and promotion of melanogenesis by rare earth elements.

DISCLOSURE

Technical Problem

In order to solve various problems of art-known hair regrowth agents, the present inventors have performed extensive studies to develop an improved agent for preventing hair loss, promoting hair regrowth and hair growth, removing and preventing dandruff, and promoting black hair formation, which is safe to the human body and has no side effect. As a result, they have surprisingly found that at least one rare earth element is extremely effective for the above-mentioned uses, and completed the present invention.

Accordingly, a first object of the present invention is to provide a composition for preventing hair loss, promoting hair regrowth and hair growth, removing and preventing dandruff, or promoting black hair formation, which contains at least one rare earth element.

A second object of the present invention is to provide uses of at least one rare earth element for preventing hair loss, promoting hair regrowth and hair growth, removing and preventing dandruff, or promoting black hair formation.

A third object of the present invention is to provide a method for preventing hair loss, promoting hair regrowth and hair growth, removing and preventing dandruff, or promoting black hair formation, by using at least one rare earth element.

A fourth object of the present invention is to provide a method for preparing an agent for preventing hair loss, promoting hair regrowth and hair growth, removing and preventing dandruff, or promoting black hair formation, by using at least one rare earth element.

Technical Solution

One aspect of the present invention relates to a composition for preventing hair loss, promoting hair regrowth and hair growth, removing and preventing dandruff, or promoting black hair formation, comprising, as an active ingredient, rare earth element selected from the group consisting of cerium (Ce), praseodymium (Pr), promethium (Pm), europium (Eu), terbium (Tb), dysprosium (Dy), holmium (Ho), erbium (Er), thulium (Tm), ytterbium (Yb), scandium (Sc), yttrium (Y), lanthanum (La), neodymium (Nd), samarium (Sm), gadolinium (Gd), lutetium (Lu) and mixtures thereof, or a salt or an oxide thereof.

Another aspect of the present invention relates to a use for preventing hair loss, promoting hair regrowth and hair growth, removing and preventing dandruff, or promoting black hair formation, of rare earth element selected from the group consisting of cerium (Ce), praseodymium (Pr), promethium (Pm), europium (Eu), terbium (Tb), dysprosium (Dy), holmium (Ho), erbium (Er), thulium (Tm), ytterbium (Yb), scandium (Sc), yttrium (Y), lanthanum (La), neodymium (Nd), samarium (Sm), gadolinium (Gd), lutetium (Lu) and mixtures thereof, or a salt or an oxide thereof.

Still another aspect of the present invention relates to a method for preventing hair loss, promoting hair regrowth and hair growth, removing and preventing dandruff, or promoting black hair formation, comprising the step of applying rare earth element selected from the group consisting of cerium (Ce), praseodymium (Pr), promethium (Pm), europium (Eu), terbium (Tb), dysprosium (Dy), holmium (Ho), erbium (Er), thulium (Tm), ytterbium (Yb), scandium (Sc), yttrium (Y), lanthanum (La), neodymium (Nd), samarium (Sm), gadolinium (Gd), lutetium (Lu) and mixtures thereof, or a salt or an oxide thereof to a subject in need thereof.

More still another aspect of the present invention relates to a method for preparing an agent for preventing hair loss, promoting hair regrowth and hair growth, removing and preventing dandruff, or promoting black hair formation, by using rare earth element selected from the group consisting of cerium (Ce), praseodymium (Pr), promethium (Pm), europium (Eu), terbium (Tb), dysprosium (Dy), holmium (Ho), erbium (Er), thulium (Tm), ytterbium (Yb), scandium (Sc), yttrium (Y), lanthanum (La), neodymium (Nd), samarium (Sm), gadolinium (Gd), lutetium (Lu) and mixtures thereof, or a salt or an oxide thereof.

The term "prevention of hair loss" as used herein means prevention, inhibition, retardation and reduction of partial or complete hair loss.

The term "promotion of hair regrowth" as used herein is defined to include maintenance, induction, stimulation, promotion and restoration of hair generation, growth of deficient hair, or extension of anagen in hair growth cycle.

The term "hair growth" as used herein is defined to include prevention of loss and promotion of development and growth of vellus hair, and conversion of vellus hair into terminal hair.

As used herein, the term "hair loss" or "alopecia" means deficiency of hair growth and partial or complete loss of hair, and includes, but is not limited to, androgenic alopecia or male pattern alopecia, toxic alopecia, alopecia areata, telogen effluvium, alopecia due to endocrine abnormality, a metabolic disorder or malnutrition, drug-induced alopecia, mechanical alopecia, alopecia accompanied by skin disorders, cicatricial alopecia, congenital alopecia and trichotillomania.

Rare earth elements share similar physicochemical properties, and kinds of rare earth elements which can be used in the present invention are not specifically limited, and any one of rare earth elements may be used alone or in admixture with other rare earth elements. Preferably, cerium (Ce) is used. A salt of rare earth element may also be used as long as it is non-toxic which is pharmaceutically or cosmetically acceptable. Examples thereof include, but are not limited to, sulfate, nitrate, carbonate, acetate, phosphate, chloride, etc. Further, an oxide of rare earth element (for example, $Ce_2O_3$, $La_2O_3$, etc.) may also be used without limit as long as it is non-toxic which is pharmaceutically or cosmetically acceptable. In the present invention, the oxide of rare earth element includes hydroxide of rare earth element (for example, $Ce(OH)_3$, $La(OH)_3$, etc.).

For use in the present invention, rare earth elements may be pulverized into fine powder, and may be contained in 0.0001 to 10% by weight, particularly 0.001 to 10% by weight, more particularly 0.001 to 0.1% by weight.

The composition of the present invention may further comprise one or more pharmaceutically or cosmetically acceptable carriers. The composition of the present invention may be prepared using any equipment or method which is commonly used or well known in pharmaceutics and cosmetics (for example, Remington's Pharmaceutical Science, 15'th Edition, 1975, Mack Publishing .Company, Easton, Pa. 18042 (Chapter 87: Balug, Seymour)). The composition of the present invention generally comprises a base and, if necessary, other ingredients used for medicines or cosmetics may be suitably added thereto. As the base for the composition of the present invention, any conventional one may be used, and examples include purified water, mineral water, ethanol, glycerin, squalene, 1,3-propylene glycol, 1,3-buthylene glycol, castor oil, tsubaki oil and liquid petrolatum. Examples of other ingredients which are added to the composition of the present invention include, but are not limited to, surfactant, emulsifier, thickener, preservative, antioxidant and flavor.

The surfactant may be cationic, anionic or non-ionic. Examples of cationic surfactant include alkaline salts (for example, sodium chloride, potassium chloride, ammonium chloride and triethanolamine chloride) of higher fatty acid such as lauric acid, myristic acid, palmitic acid, stearic acid, oleic acid, etc.; salts of alkylsulfuric ester such as sodium lauryl sulfate, triethanolamine lauryl sulfate, etc.; and salts of alkyl ether sulfuric ester such as sodium polyoxyethylene lauryl ether sulfate, triethanolamine polyoxyethylene lauryl ether sulfate, etc. Examples of non-ionic surfactant include polyoxyethylene alkyl ethers such as polyoxyethylene lauryl ether, polyoxyethylene oleyl ether, etc.; and alkanol amide such as coconut oil fatty acid diethanol amide, lauric acid diethanol amide, etc. Examples of anionic surfactant include stearyl trimethyl ammonium chloride, cetyl trimethyl ammonium chloride and stearyl bis(diethyl alcohol) hydroxyethyl ammonium chloride.

Examples of emulsifier include cethanol, stearyl alcohol and behenyl alcohol.

Examples of thickener include sodium alginate, methylcellulose, carboxymethylcellulose, polyvinylalcohol and polyvinylpyrrolidone.

Examples of preservative include ethyl parahydroxybenzoate, butyl parahydroxybenzoate and benzalkonium chloride.

Examples of antioxidant include butylhydroxytoluene, propyl gallate and butylhydroxyanisole.

Flavors may be a commonly used perfume, examples of which include citrus, lavender and floral.

In addition to the above-mentioned ingredients, the composition of the present invention may further comprise at least one sugar including monosaccharide such as glucose, xylose, mannose, arabinose, etc. and disaccharide such as maltose, sucrose, cellobiose, trehalose, etc., which can act to supply nutrients to hair follicle. An amount thereof is preferably 0.01 to 1% by weight based on the total weight of the composition. Further, the composition of the present invention may further comprise one or more conventionally used auxiliaries for promoting hair growth, examples of which include one or more selected from the group consisting of ginseng, *Sophora flavescens*, peels of *Citrus unshiu*, green tea, carrot, platycodon, *Mori Fructus, Rhynchosia Volubilis*, punica grantum, pine needles, seed of evening primrose, needles of *Thuja orientalis*, knotgrass, *Eclipta prostrate, Tribulus* extract, betaine, peppermint extract, nettle extract, horsetail extract, lavender extract, hop extract, aloe, *Acanthopanax senticosus*, vegetable worms, *Rubus Coreanus*, mulberry, Poroligenous liquor, bamboo salt, *Astragalus membranaceus, Angelica gigas*, Chinese matrimony vine, walnut, grape, safflower, sesame, *perilla* seeds, garlic, kelp, brown seaweed, Japanese apricot, mung beans, *Oryza sativa*, pentadecanoic acid glyceride, hinokitiol, *capsicum* tincture, ginger tincture, cantharis tincture, forskolin, trans-3,4'-dimethyl-3-hydroxyflavanone, tocopherols such as tocopherol acetate, etc., nicotinic acid, nicotinic amide, retinol palmitate, β-carotene, calciferol, folic acid, biotin, D-pantothenyl alcohol, acetyl pantothenyl ethyl ether, calcium pantothenate, pantothenyl ethyl ether, ascorbic acid, grapefruit seed extract, cepharanthin, nicotinic benzyl ester, vitamins A, $B_1$, $B_2$, $B_6$ (pyridoxine) and derivatives thereof, pantothenic acid and derivatives thereof, minoxidil, extract of *Swertia* pseudo-chinensis, arginine, aspartic acid, methionine, serine, glycine, glutamic acid, cystine, amino acid extract, β-glycyrrhetinic acid, glycyrrhizic acid, pyridoxine hydrochloride, salicylic acid, allantoin, photosensitizer 301, isopropylmethylphenol, picrotone olamine, glycerin, pyrrolidone carboxylic acid, estradiol, ethinyl estradiol and l-menthol. An amount thereof is preferably 0.0001 to 10% by weight of the total weight of the composition.

Rare earth elements such as lanthanum (La), neodymium (Nd), samarium (Sm), gadolinium (Gd) or lutetium (Lu), in combination with *capsicum* tincture, have a synergistic effect to give more superior effects of preventing hair loss, promoting hair regrowth and hair growth, and removing and preventing dandruff, by decreasing TGF-β expression and increasing VEGF expression, as well as promoting black hair formation by promoting expression and activity of tyrosinase, and melanin production. As long as the desired synergistic effect can be obtained, the combined ratio between the two ingredients is not particularly limited, but it is preferable to contain rare earth element and *capsicum* tincture in the weight ratio of 1:0.0001~1, particularly 1:0.01~1, more particularly 1:0.1~1. This is because the desired synergistic effect can be maximized within the range, but the scope of the present invention is not limited to the specific range. Furthermore, the present composition may further comprise ginger tincture and/or cantharis tincture. Ginger tincture is a tincture which is obtained by extracting rhizome of ginger (*Zingiber officinale* roscoe) with ethanol, and it is known that its pungent ingredients, zingerone, shogaol, etc. stimulate hair root to promote hair regrowth. Cantharis refers to insects of Meloidae, and the cantharis tincture is obtained by extraction of the insects with ethanol.

A subject for application of the composition of the present invention is not particularly limited, and the composition of the present invention may be applied to humans as well as all animals including farm animals and pet animals.

The composition of the present invention may be transdermally or orally administered, and for this purpose, may be formulated into lotion, ointment, cream, patch, spray, tablet, pill, powder, sachet, elixir, suspension, emulsion, solution, syrup, or soft or hard capsule.

Particularly, the composition of the present invention may be used by directly spreading or spraying it. Hairs to which the composition of the present invention is applied include hair root, hair follicle and hair on the head, eyebrows and eyelashes, beard, mustache, whiskers, axillary hair, as well as any regions of body having hair root and hair follicle. Therefore, the present invention may be used as hair tonic, hair lotion, hair cream, hair spray, hair mousse, hair gel, hair conditioner, hair shampoo, hair rinse, hair pack, hair treatment, eyebrow regrowth agent, eyelash regrowth agent or nutrients for eyelashes, or shampoo and rinse for pet animals.

A dosage of rare earth element according to the present invention should be appropriately determined considering sex, age, condition of alopecia, condition of hair, etc. Generally, a daily dosage for an adult is about 0.1 to about 5 mg/cm², which may be applied 1 to 5 times a day.

DESCRIPTION OF DRAWINGS

The above and other objects, features and advantages of the present invention will become apparent from the following description of preferred embodiments given in conjunction with the accompanying drawings, in which.

BEST MODE

Figure 1:
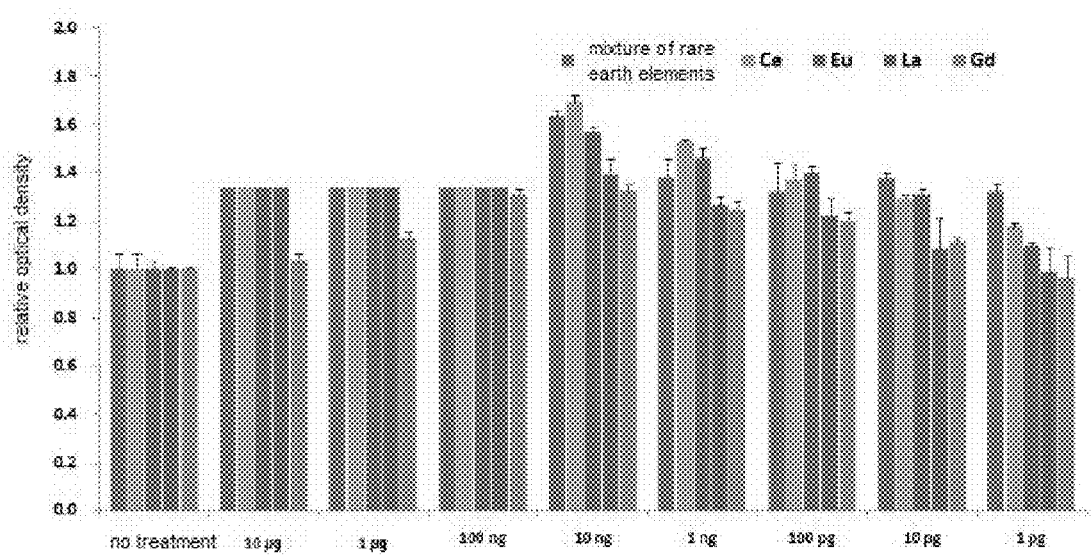
FIG. 1 is a graph showing the effect of promoting cell proliferation of various concentrations of each element.

Hereinafter, the present invention will be specifically described with reference to examples, but they should not be construed to limit the scope of the present invention in any manner.

EXAMPLE 1

Preparation of a Composition for Hair Improvement

Using the ingredients and the amounts shown in Table 1, mixed powder of rare earth elements was mixed homogeneously with other ingredients, and then, the mixture was filtered to prepare the composition for hair improvement. The prepared composition for hair improvement was light brown and opaque, and had pH of 5.0 to 8.5.

TABLE 1 ingredients and amounts of composition for hair improvement

| | Ingredient | Amount (% by weight) Example 1 |
|---|---|---|
| 1 | Mixed rare earth elements | 0.001 |
| 2 | α-tocopherol | 0.1 |
| 3 | Salicylic acid | 0.1 |
| 4 | Menthol | 0.1 |
| 5 | Ethanol | 60 |
| 6 | Propylene glycol | 2 |
| 7 | Purified water | ad 100 |

EXAMPLECL EXAMPLES 2 to 18

Preparation of Compositions for Hair Improvement

The compositions for hair improvement were prepared according to substantially the same process as in Example 1, except that individual rare earth elements, i.e. Ce (Example 2), Pr (Example 3), Pm (Example 4), Eu (Example 5), Tb (Example 6), Dy (Example 7), Ho (Example 8), Er (Example 9), Tm (Example 10), Yb (Example 11), Sc (Example 12), Y (Example 13), La (Example 14), Nd (Example 15), Sm (Example 16), Gd (Example 17) and Lu (Example 18) were used, respectively, instead of mixed rare earth elements.

EXAMPLE 19

Preparation of a Composition for Hair Improvement

The composition for hair improvement was prepared according to substantially the same process as in Example 1, except that 0.1% by weight of mixed powder of La, Nd, Sm and Lu was used instead of mixed powder of rare earth elements, and 0.001% by weight of *capsicum* tincture was further used. The prepared composition for hair improvement was light brown and opaque, and had pH of 5.0 to 8.5.

EXAMPLECL EXAMPLES 20 to 24

Preparation of Compositions for Hair Improvement

The compositions for hair improvement were prepared according to substantially the same process as in Example 19, except that individual rare earth elements, i.e. La (Example 20), Nd (Example 21), Sm (Example 22), Gd (Example 23) and Lu (Example 24) were used, respectively, instead of mixed powder of La, Nd, Sm and Lu.

COMPARATIVE EXAMPLE

A composition was prepared according to substantially the same process as in Example 1, except that mixed powder of rare earth elements was not used.

EXPERIMENTAL EXAMPLE 1

Evaluation of the Effect of Promoting Cell Proliferation of Rare Earth Elements

Mouse embryo fibroblasts NIH 3T3 were cultivated in an incubator at 37° C. (95% $O_2$, 5% $CO_2$ and 60% humidity) while maintaining a density of $2 \times 10^6$ or $4 \times 10^6$ cells/ml in Dulbecco's modified Eagle's media (DMEM) supplemented with 10% fetal bovine serum (FBS) and 1% penicillin-streptomycin. Cell proliferation was measured by using MTT [3-(3,5-dimethyl-thiazol-2-yl)-2,5-diphenyltetrazolium bromide] assay. For MTT assay, the cells were plated in a 96-well plate at $2 \times 10^3$ cells/ml per well, and treated with a culture medium supplemented with 10% FBS. The cells were stabilized in the incubator for 24 hours, the culture medium supplemented with FBS was replaced by FBS-free DMEM, and the cells were treated with mixed rare earth elements of 10 μg, 1 μg, 100 ng, 10 ng, 1 ng, 100 pg, 10 pg and 1 pg, respectively, and individual rare earth elements of 10 ng. Then, the cells were cultivated for a given time, 50 μl per well of MTT (2 mg/l ml sterilized distilled water) was added thereto, and the mixture was reacted for 4 hours. The reaction mixture was treated with DMSO (dimethyl sulfoxide) and shaken for 30 minutes. Absorbance was measured at 540 nm using an ELISA reader (550, Bio-rad).

Figure 2:
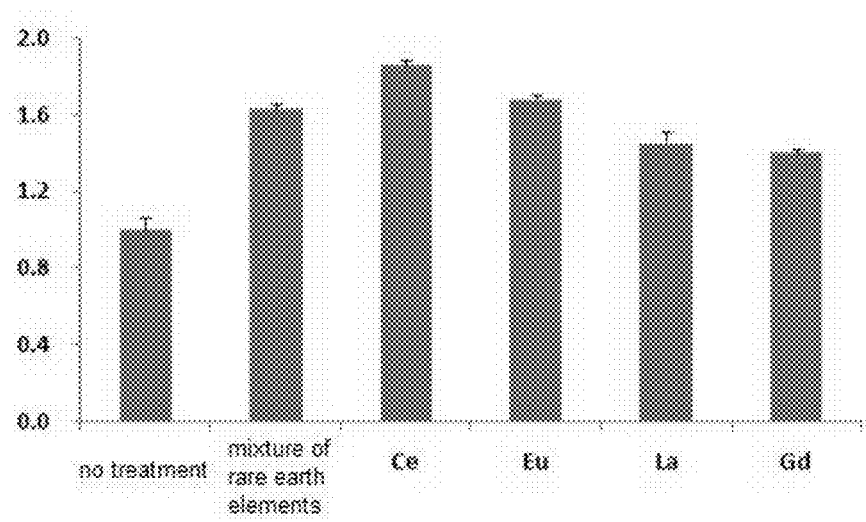
FIG. 2 is a graph showing the effect of promoting cell proliferation of mixed and individual rare earth elements at a constant concentration.

The results of treatment with various concentrations of each element (mixed rare earth elements, Ce, Eu, La, Gd) are shown in FIG. 1, and the results of treatment with each element at a constant concentration are shown in FIG. 2. As shown in FIG. 1, it was found that cell proliferation was increased in the groups treated with each element of 10 μg to 1 pg compared with the non-treated group. Particularly, cerium increased cell proliferation up to 1.69 times compared with the non-treated group. Thus, it was concluded that each element influenced cell proliferation. In addition, as shown in FIG. 2, it was found that in the groups treated with each element of 10 ng, cell proliferation was increased compared with the non-treated group, and cerium (Ce), praseodymium (Pr), promethium (Pm), europium (Eu), terbium (Tb), dysprosium (Dy), holmium (Ho), erbium (Er), thulium (Tm), ytterbium (Yb), scandium (Sc) and yttrium (Y) showed the similar effects. Particularly, in the group treated with cerium (Ce), cell proliferation was the most greatly increased. On the contrary, lanthanum (La), neodymium (Nd), samarium (Sm), gadolinium (Gd) and lutetium (Lu) showed a relatively inferior effect.

EXPERIMENTAL EXAMPLE 2

Evaluation of the Effect of Promoting Cell Proliferation in Animals

Before initiation of the experiment, 6 week-aged male C57BL6 mice (29±3 g) were supplied with pellets (Samyang Co.) and water ad libitum. For acclimation, they were preliminarily bred in a polypropylene box (453×293×247(H) mm, 19 l) for a week (20~24° C., 60~80% humidity). Then, the mice were depilated at a predetermined area ($3 \times 5$ cm$^2$) on the dorsal side, and randomly divided into a group treated with the composition of Comparative Example (control group), a group treated with the composition of Example 1, and a group treated with the composition of Example 2 (experimental groups). Each group was maintained under a light/darkness cycle of 12 hours. The compositions prepared according to Examples 1 and 2 and Comparative Example were applied twice a day (on given times in the morning and the evening) at a constant amount (1 ml). In all experiments, the mice were allowed to rest without performing experiments under the darkness, and upon the collection of tissue, they were allowed to restore for 24 hours.

Figure 3:
FIG. 3 is a photograph showing the effect of promoting hair regrowth of the composition according to the present invention in animals.
Figure 3:
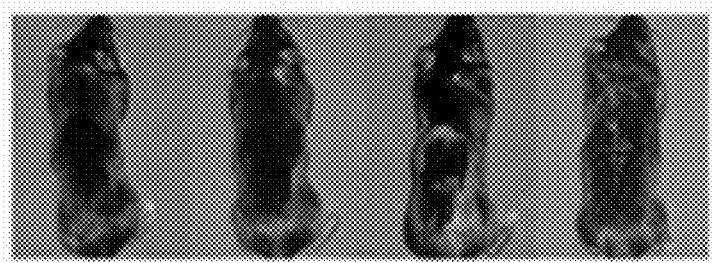
Figure 3:

The results are shown in FIG. 3. As shown in FIG. 3, in the groups treated with the compositions of Examples 1 and 2, it was found that hairs were growing with the lapse of time. In the groups treated with the compositions of Examples 1 and 2, hair growth rate is much faster, the number of hairs is much larger, and hairs are thicker and glossier than in the group treated with the composition of Comparative Example. A significant difference was found between the experimental groups and the control group since hair growth rate became much faster from 20th day after the initiation of treatment. Particularly, the composition of Example 2 containing cerium showed the similar effect to that of Example 1 containing mixed rare earth elements.

EXPERIMENTAL EXAMPLE 3

Observation of Skin Tissue of Animals

The mice of Example 2 were sacrificed with cervical dislocation, their skin was isolated, and impurities were removed as much as possible with phosphate buffered saline (PBS). An experimental region was cut out with scissors, and used in the following experiment. The isolated skin was fixed in 10% formaldehyde for a day, cut into a size of 10 mm$^2$, and penetrated in an auto-penetrator for 12 hours to prepare a paraffin block. Then, the paraffin block was sectioned to a thickness of 4 μm using a microtome, and stained with hematoxylin and eosin. Reading and photographing were conducted under an optical microscope with 100× magnification.

Figure 4:
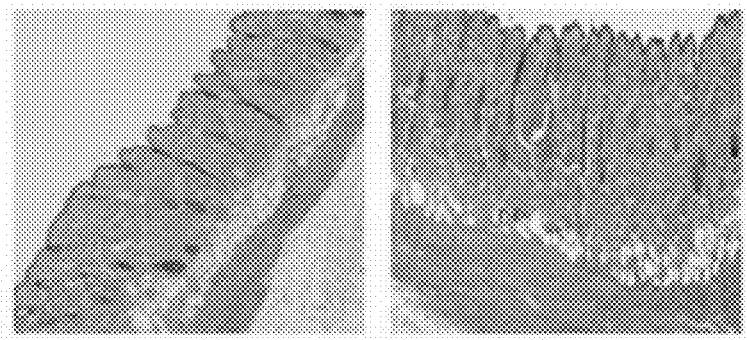
FIG. 4 is a micrograph showing animal skin tissues treated with the composition according to the present invention.
Figure 4:
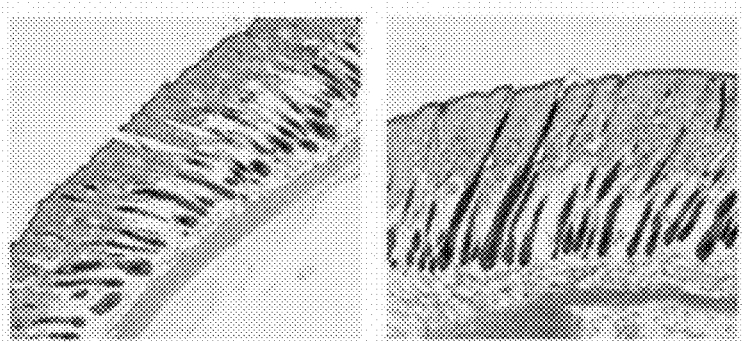
Figure 4:
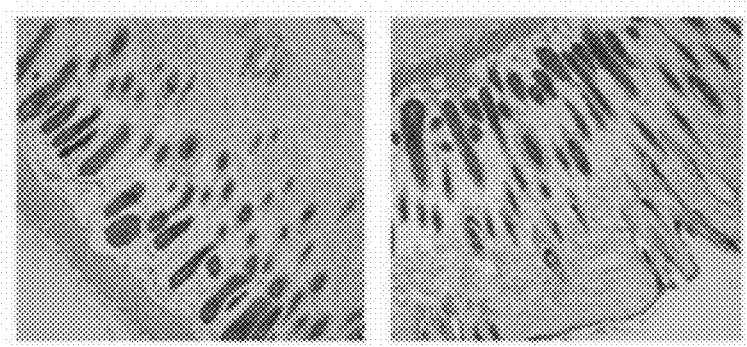

The results are shown in FIG. 4. As shown in FIG. 4, it was found that the experimental group treated with the compositions of Examples 1 and 2 showed a significant difference in hair growth from the control group treated with the composition of Comparative Example. That is, hair follicles were generated in skin and adipose tissues and dermis, and grown towards epidermis in the experimental groups, while hair growth was just initiated in the control group. It was also found that the experimental groups had the larger number of hair follicles than the control group. Particularly, the composition of Example 2 containing cerium showed the similar effect to the composition of Example 1 containing mixed rare earth elements. For reference, mice have hairs of synchronistic type in which all hairs have a synchronized cycle, while humans have hairs of mosaic type in which each hair has different cycles.

EXPERIMENTAL EXAMPLE 4

Measurement of the Expression of TGF-β2 and VEGF

TGF-β, which has isoforms, is a multipotent cytokine that regulates early development; cell cycle; proliferation, differentiation, migration and survival of cells; production of extracellular matrix; immune system; formation of blood vessel and blood cells; induction of apoptosis; skeletal formation; and wound healing in various kinds of cells and tissues. It is known that TGF-β is expressed in catagen of hair growth cycle to induce apoptosis of hair cells. Vascular endothelial growth factor (VEGF) is a glycoprotein having isoforms, and is the most general and effective growth factor, which is known to stimulate angiogenesis in wounds and is expressed in many blood vessel tissues. It is known as a mitogen which is specific for epithelial cells to induce migration and proliferation of epithelial cells and to increase the penetrability of blood vessel. VEGF is believed to be involved in hair regrowth by minoxidil previously commercialized, and to promote hair growth by increasing blood flow from vasodilatory action in dermal papilla, a major cell constituting hair follicle, and supplying nutrients to hair root.

In order to measure the expression of the above factors by Western blotting, proteins were obtained from the tissue of the experimental animals of Example 3, and resolved on 12% SDS-PAGE and transferred to nitrocellulose membrane (NC). The group treated with the composition of Example 14 containing lanthanum was added to the groups of Examples 2 and 3. Then, the NC was blocked with Tris buffered saline (TBS) containing 5% skim milk, and reacted with a primary antibody diluted to 1:1,000 (anti-TGF-β2 and anti-VEGF rabbit IgG) and a secondary antibody diluted to 1:1,000 (peroxidase-conjugated anti-rabbit IgG), respectively. Then, it was washed with TBS containing 0.05% Tween-20, and photosensitized on an X-ray film using an ECL detection kit. Then, OD values were graphed using an image analysis program of LabWork™ (version 4.4.00.0).

Figure 5:
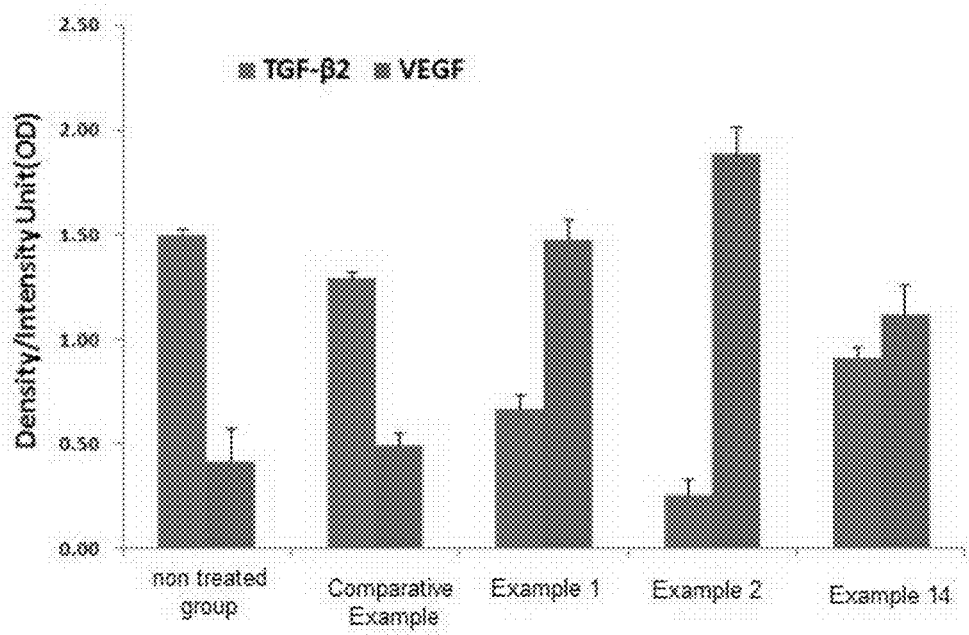
FIG. 5 is a graph showing the expression of TGF-β2 and VEGF in animal tissues treated with the composition according to the present invention.

The results are shown in FIG. 5. As shown in FIG. 5, it was found that the expression of TGF-β2 was significantly decreased in the group treated with the compositions of Examples 1, 2 and 14 (experimental groups) compared with in the group treated with the composition of Comparative Example (control group). Further, it was found that more VEGF was expressed in the experimental groups than in the control group. That is, the composition for hair improvement of the present invention decreases the activity of TGF-β2 and increases the activity of VEGF, and thus, inhibits apoptosis of hair follicle cells by TGF-β2, and supplies nutrients to hair root by increasing blood flow from vasodilatory action to promote hair growth, thereby showing effects of preventing hair loss and promoting hair growth. Particularly, the group treated with the composition of Example 2 containing cerium showed the superior effect to the group treated with the composition of Example 1 containing mixed rare earth elements. On the contrary, the group treated with the composition of Example 14 containing lanthanum showed a superior effect to the non-treated group, but showed an inferior effect to the group treated with the composition of Example 1 or 2.

EXPERIMENTAL EXAMPLE 5

Evaluation of the Effect of Promoting Hair Regrowth and Black Hair Formation in Humans Ten of thirty male and female patients suffering from various kinds of alopecia were treated with the composition of Example 1, the composition of Example 2 and the composition of Comparative Example, respectively, and then, their effectiveness was evaluated. Administration to scalp was performed twice a day, every day for 2 months, and condition of hair growth was evaluated after 1 month and 2 months. The standard for evaluation was as follows:
1. Highly effective—Neonatal terminal hairs are shown.
2. Intermediately effective—Neonatal vellus hairs are shown.
3. Little effective—Hair loss is decreased.
4. Dandruff is reduced.

The results are shown in Tables 2 and 3.

TABLE 2

| | | | Hair regrowth effect in humans | | | |
|---|---|---|---|---|---|---|
| | Testee | Month | Neonatal hairs (terminal) | Neonatal hairs (vellus) | Reduction of hair loss | Reduction of dandruff |
| Example 1 | 1 | After 1 month | − | + | ++ | ++ |
| | | After 2 months | + | ++ | ++ | ++ |
| | 2 | After 1 month | + | + | ++ | ++ |
| | | After 2 months | ++ | ++ | ++ | ++ |

TABLE 2-continued

Hair regrowth effect in humans

| Testee | Month | Neonatal hairs (terminal) | Neonatal hairs (vellus) | Reduction of hair loss | Reduction of dandruff |
|---|---|---|---|---|---|
| 3 | After 1 month | − | + | ++ | ++ |
|  | After 2 months | + | ++ | ++ | ++ |
| 4 | After 1 month | − | ++ | ++ | ++ |
|  | After 2 months | ++ | ++ | ++ | ++ |
| 5 | After 1 month | + | + | ++ | ++ |
|  | After 2 months | ++ | ++ | ++ | ++ |
| 6 | After 1 month | − | + | ++ | ++ |
|  | After 2 months | + | ++ | ++ | ++ |
| 7 | After 1 month | + | + | ++ | ++ |
|  | After 2 months | ++ | ++ | ++ | ++ |
| 8 | After 1 month | − | + | ++ | ++ |
|  | After 2 months | + | ++ | ++ | ++ |
| 9 | After 1 month | − | ++ | ++ | ++ |
|  | After 2 months | ++ | ++ | ++ | ++ |
| 10 | After 1 month | + | + | ++ | ++ |
|  | After 2 months | ++ | ++ | ++ | ++ |

Example 2

| Testee | Month | Neonatal hairs (terminal) | Neonatal hairs (vellus) | Reduction of hair loss | Reduction of dandruff |
|---|---|---|---|---|---|
| 1 | After 1 month | + | ++ | ++ | ++ |
|  | After 2 months | + | ++ | ++ | ++ |
| 2 | After 1 month | + | + | ++ | ++ |
|  | After 2 months | ++ | ++ | ++ | ++ |
| 3 | After 1 month | − | + | ++ | ++ |
|  | After 2 months | + | ++ | ++ | ++ |
| 4 | After 1 month | − | ++ | ++ | ++ |
|  | After 2 months | ++ | ++ | ++ | ++ |

TABLE 2-continued

| | | Hair regrowth effect in humans | | | |
|---|---|---|---|---|---|
| Testee | Month | Neonatal hairs (terminal) | Neonatal hairs (vellus) | Reduction of hair loss | Reduction of dandruff |
| 5 | After 1 month | + | + | ++ | ++ |
| | After 2 months | ++ | ++ | ++ | ++ |
| 6 | After 1 month | + | + | ++ | ++ |
| | After 2 months | + | ++ | ++ | ++ |
| 7 | After 1 month | + | ++ | ++ | ++ |
| | After 2 months | ++ | ++ | ++ | ++ |
| 8 | After 1 month | − | + | ++ | ++ |
| | After 2 months | + | ++ | ++ | ++ |
| 9 | After 1 month | + | ++ | ++ | ++ |
| | After 2 months | ++ | ++ | ++ | ++ |
| 10 | After 1 month | + | ++ | ++ | ++ |
| | After 2 months | ++ | ++ | ++ | ++ |

(Excellent: ++, Good: +, No change: −, Worsen: −−)

TABLE 3

| | Testee | Month | Neonatal hairs (terminal) | Neonatal hairs (vellus) | Reduction of hair loss | Reduction of dandruff |
|---|---|---|---|---|---|---|
| Comparative Example | 1 | After 1 month | − | − | − | − |
| | | After 2 months | − | + | − | − |
| | 2 | After 1 month | − | − | − | − |
| | | After 2 months | − | − | + | + |
| | 3 | After 1 month | − | − | − | − |
| | | After 2 months | − | − | − | − |
| | 4 | After 1 month | − | − | − | − |
| | | After 2 months | − | + | + | + |

TABLE 3-continued

| Testee | Month | Neonatal hairs (terminal) | Neonatal hairs (vellus) | Reduction of hair loss | Reduction of dandruff |
|---|---|---|---|---|---|
| 5 | After 1 month | − | − | − | − |
|   | After 2 months | − | − | − | − |
| 6 | After 1 month | − | − | − | − |
|   | After 2 months | − | − | + | − |
| 7 | After 1 month | − | − | − | − |
|   | After 2 months | − | − | − | + |
| 8 | After 1 month | − | − | − | − |
|   | After 2 months | − | − | − | + |
| 9 | After 1 month | − | − | − | − |
|   | After 2 months | − | + | − | − |
| 10 | After 1 month | − | − | − | − |
|   | After 2 months | − | − | + | −− |

(Excellent: ++, Good: +, No change: −, Worsen: −−)

As shown in Tables 2 and 3, the compositions according to the present invention showed the effects of hair regrowth and hair growth after 1 month, and their effects were sustained after 2 months. Further, hair loss was reduced within 1 week to 2 weeks after the compositions of Example 1 and Example 2 had been spread. Despite individual variation, dandruff was reduced within 5 to 7 days after the compositions had been spread, and dandruff and head itching completely disappeared with the lapse of time. In addition, it was confirmed with naked eyes that black hairs were formed in males and females having white hairs among the testees. As can be seen from the above results, the composition of the present invention has a little individual variation in time and degree of hair regrowth, and is highly effective for alopecia. In addition, in all testees, thickness of hairs was increased and formation of black hairs was promoted. No side effect was observed. In the group treated with the composition of Comparative Example, growth of vellus hair, reduction of hair loss or removal of dandruff was shown, but was not significant.

Figure 6:
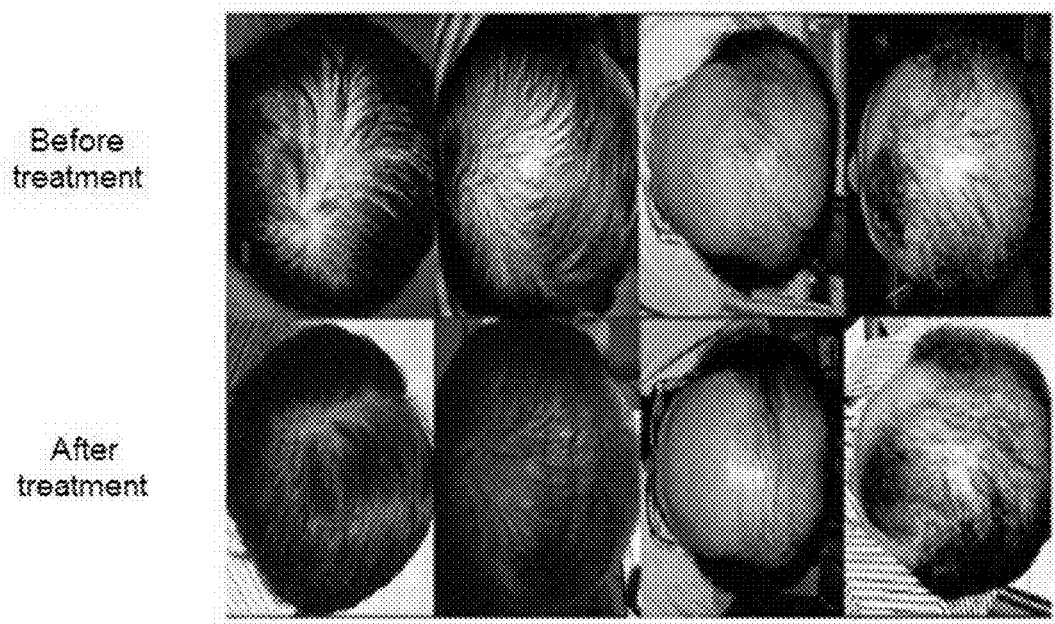
FIG. 6 is a photograph showing the effect of promoting hair regrowth of the composition according to the present invention in humans.

Heads of 40- to 47-old males among the testees before and months after treatment with the composition of Example 2 were photographed, and the photographs are shown in FIG. 6. As shown in FIG. 6, the testees had begun to loose hairs and had few hairs in forehead and vertex showing signs of alopecia. They had suffered from the symptoms of serious progress of alopecia due to head itching, dandruff, stress-induced fatigue, etc. After spreading the composition of Example 2 to the scalp twice a day, head itching and dandruff disappeared from third day and hair loss was significantly decreased. From 1 month after spreading, vellus hairs were started to grow at the hair-loosed region of forehead or vertex, and then, continuously grew to be observed with naked eyes after 2 months. From the above results, it can be concluded that the composition of the present invention has excellent hair growth effect and is non-toxic to human body even with long-term use.

EXPERIMENTAL EXAMPLE 6

Measurement of the Activity of Tyrosinase for Evaluation of the Effect of Promoting Black Hair Formation In order to evaluate the effect of promoting black hair formation, the activity of tyrosinase was measured in Sk-mel-31, a human melanoma cell, and B16F10, a mouse melanoma cell. The cells were cultivated in an incubator at 37° C. (5% $CO_2$ and 60% relative humidity) while maintaining a density of $1\times10^6$ cells/ml for Sk-mel-31 and $2\times10^5$ cells/ml for B16F10 in RPMI-1640 medium (containing 1% penicillin-streptomycin and 10% fetal bovine serum). The cells were stabilized in the incubator for 24 hours, and the culture medium containing FBS was replaced by FBS-free RPMI-1640. The cells were treated with mixed rare earth elements of 10 μg, 1 μg, 100 ng, 10 ng, 1 ng, 100 pg, 10 g and 1 pg, respectively, and individual rare earth elements of 10 ng. In order to measure the activity of tyrosinase, the cells were cultivated for a given time, centrifuged (100×g) for 10 minutes, and harvested. The harvested cells were sonicated in 0.01 M sodium phosphate buffer (containing 1% Triton X-100 and 0.1 mM phenylmethyl sulfonyl fluoride (PMSF), pH 7.4). The cells were placed in an ice bath for one hour, and centrifuged with 40,000×g at 4° C. for 20 minutes to obtain a cell extract. 130 μl of 5 mM L-DOPA (L-3,4-dihydroxyphenylalanine) and 120 μl of 25 mM MBTH (3-methyl-2-benzothiazolinone hydrazone) were added to 250 μl of an analysis buffer containing 100 mM potassium phosphate (pH 7.1), 4% N,N-dimethylformamide and 0.1% (v/v) Triton X-100, and reacted in a thermostat at 37° C. for 5 minutes, and then, 100 μg of the cell extract was added thereto, and further reacted for 2 hours. Then, 500 μl of 1 M perchloric acid was added thereto and the mixture was centrifuged with 9,000×g at room temperature for 20 minutes. Then, the supernatant was taken and absorbance was measured at 505 nm.

Figure 7:
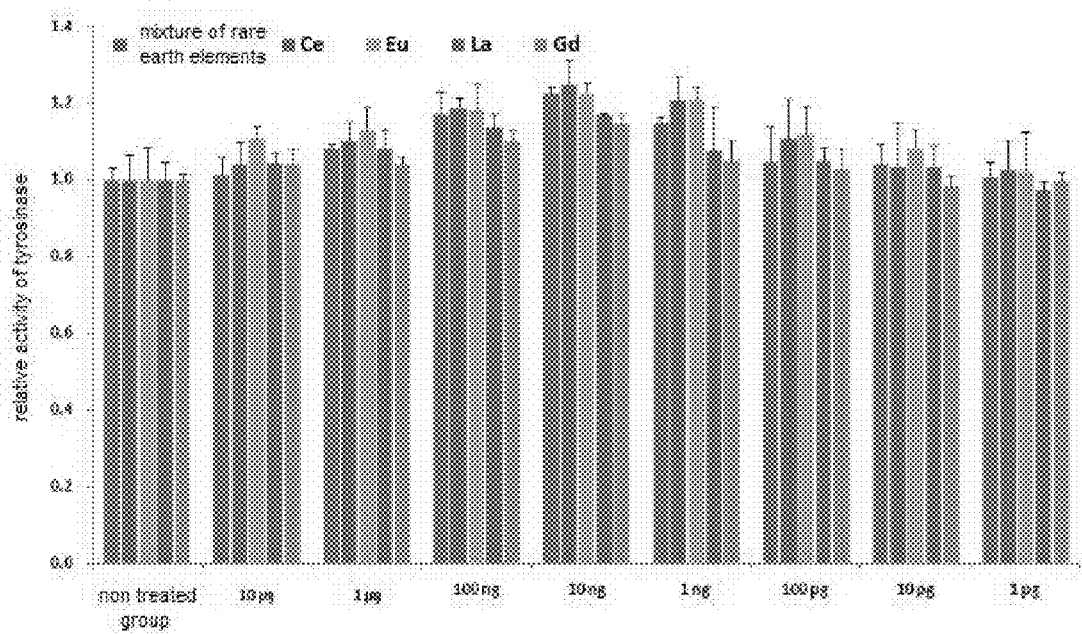
FIG. 7 is a graph showing the activity of tyrosinase in human melanoma cell lines treated with various concentrations of each element.
Figure 8:
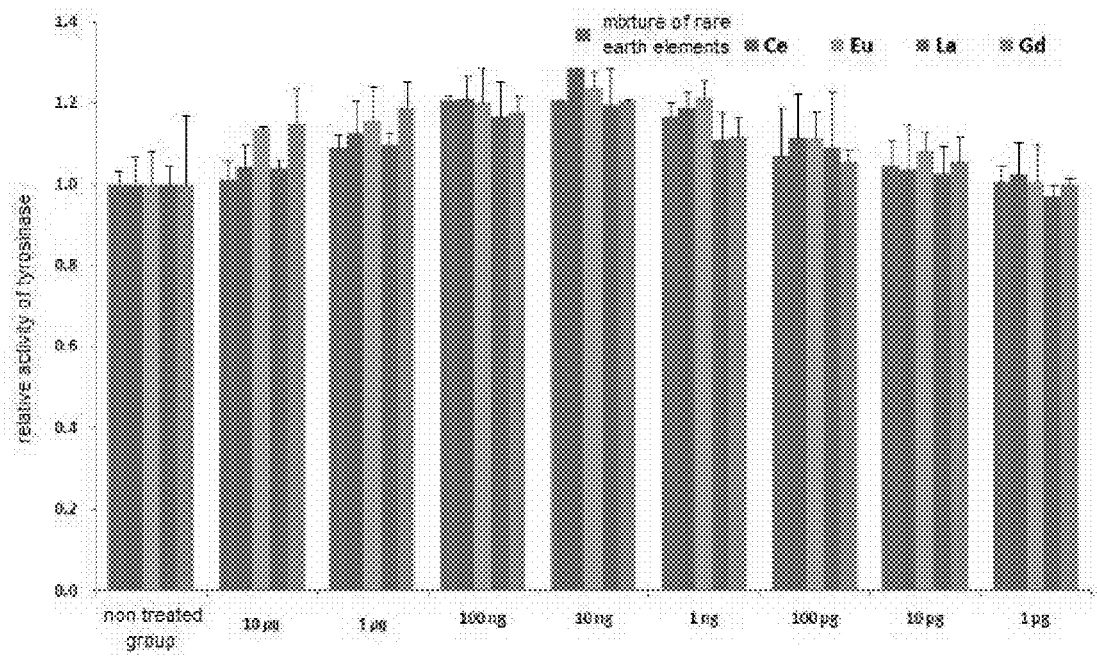
FIG. 8 is a graph showing the activity of tyrosinase in mouse melanoma cell lines treated with various concentrations of each element.

FIGS. 7 and 8 show the results of treating Sk-mel-31 and B16F10 with mixed rare earth elements and individual rare earth elements (Ce, Eu, La, Gd), respectively. As shown in FIGS. 7 and 8, it was found that tyrosinase activity was increased in the group treated with 10 μg to 1 pg of mixed rare earth elements and individual rare earth elements compared with in the control group. Thus, it could be concluded that the rare earth element influenced the activity of tyrosinase. That is, mixed and individual rare earth elements have the effect of promoting black hair formation since they increase the activity of tyrosinase to promote melanin production. It was found that individual rare earth elements, cerium (Ce), praseodymium (Pr), promethium (Pm), europium (Eu), terbium (Tb), dysprosium (Dy), holmium (Ho), erbium (Er), thulium (Tm), ytterbium (Yb), scandium (Sc) and yttrium (Y), showed substantially the same effect as mixed rare earth elements. Particularly, cerium (Ce) most greatly increased the activity of tyrosinase. Lanthanum (La), neodymium (Nd), samarium (Sm), gadolinium (Gd) and lutetium (Lu) showed relatively lower effect than the above-described elements.

EXPERIMENTAL EXAMPLE 7

Measurement of the Expression of Tyrosinase for Evaluation of Effect of Promoting Black Hair Formation Cells were cultivated according to the same process as in Experimental Example 6, and centrifuged (100×g) for 10 minutes to harvest the cells. In order to measure the expression of tyrosinase by Western blotting, 100 μg of the cell extract was resolved on 10% SDS-PAGE, transferred to NC, and then, blocked with TBS containing 5% skim milk. Then, it was reacted with a primary antibody diluted to 1:2,500 (monoclonal anti-tyrosine hydroxylase clone Th-2) and a secondary antibody diluted to 1:5,000 (anti-mouse IgG), respectively, and washed with TBS containing 0.2% Tween-20, and then, photosensitized on an X-ray film using an ECL detection kit. Then, OD values were graphed using an image analysis program of LabWork™ (version 4.4.00.0).

Figure 9:
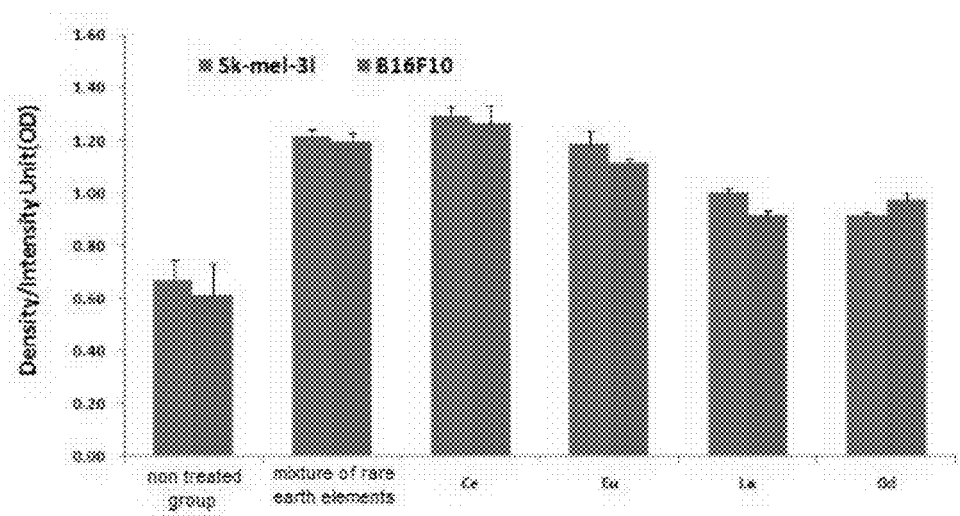
FIG. 9 is a graph showing the expression of tyrosinase in human and mouse melanoma cell lines treated with mixed and individual rare earth elements.

The results are shown in FIG. 9. As shown in FIG. 9, it was found that the expression of tyrosinase was increased in the group treated with mixed rare earth elements compared with the control group. Thus, it could be concluded that mixed rare earth elements increases the expression of tyrosinase to promote production of melanin determining hair color. It was found that the groups treated with individual rare earth elements, cerium (Ce), praseodymium (Pr), promethium (Pm), europium (Eu), terbium (Tb), dysprosium (Dy), holmium (Ho), erbium (Er), thulium (Tm), ytterbium (Yb), scandium (Sc) and yttrium (Y), showed substantially the same effect as the group treated with mixed rare earth elements. Particularly, the expression of tyrosinase was most greatly increased in the group treated with cerium (Ce). Meanwhile, it was found that lanthanum (La), neodymium (Nd), samarium (Sm), gadolinium (Gd) and lutetium (Lu) shoed relatively lower effect than the above-described elements.

EXPERIMENTAL EXAMPLE 8

Measurement of Melanin Production for Evaluation of the Effect of Promoting Black Hair Formation Cells were cultivated according to the same process as in Experimental Example 6, and centrifuged (100×g) for 10 minutes to harvest the cells. In order to measure the production of melanin, 200 μg of the cell extract was added to 1 N NaOH (total 1 ml), allowed to stand at room temperature for 30 minutes, and then, absorbance was measured at 400 nm.

Figure 10:
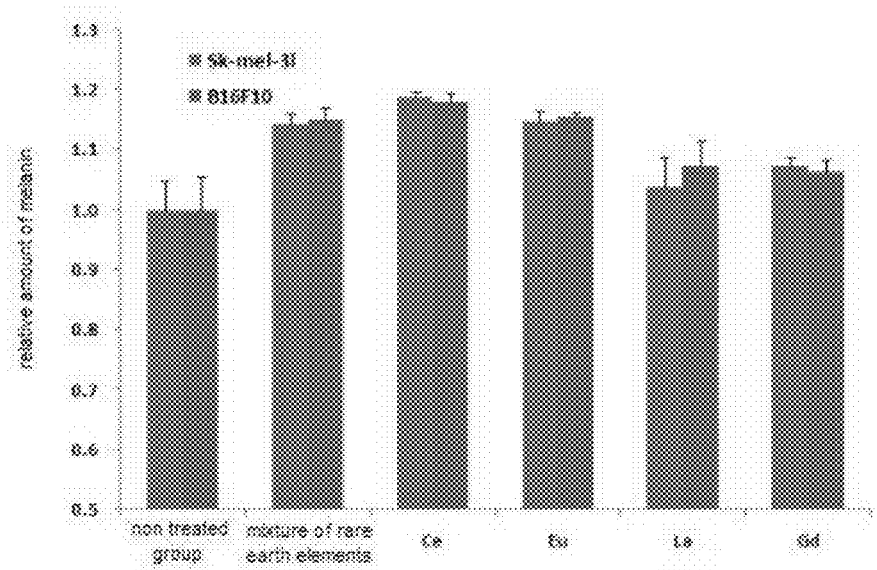
FIG. 10 is a graph showing the melanin production in human and mouse melanoma cell lines treated with mixed and individual rare earth elements.

The results are shown in FIG. 10. As shown in FIG. 10, it was found that melanin production was increased in the group treated with mixed rare earth elements compared with the control group. This suggests that increased activity and expression of tyrosinase results in increased melanin production, thereby to promote the formation of black hairs. It was found that substantially the same effect as in the group treated with mixed rare earth elements could be obtained in the groups treated with individual rare earth elements. The groups treated with individual rare earth elements, cerium (Ce), praseodymium (Pr), promethium (Pm), europium (Eu), terbium (Tb), dysprosium (Dy), holmium (Ho), erbium (Er), thulium (Tm), ytterbium (Yb), scandium (Sc) and yttrium (Y), showed substantially the same effect as the above-described ones. Particularly, the amount of melanin was most greatly increased in the group treated with cerium (Ce). Meanwhile, lanthanum (La), neodymium (Nd), samarium (Sm), gadolinium (Gd) and lutetium (Lu) showed relatively lower effect than the above-described elements.

EXPERIMENTAL EXAMPLE 9

Comparison of the Expression of TGF-β and VEGF and the Production of Melanin by Combination of Lanthanum (La), Neodymium (Nd), Samarium (Sm), Gadolinium (Gd) or Lutetium (Lu) with *Capsicum* Tincture In order to test a synergistic effect between lanthanum (La), neodymium (Nd), samarium (Sm), gadolinium (Gd) or lutetium (Lu) among rare earth elements and *capsicum* tincture, the expression of TGF-β and VEGF and the production of melanin were measured.

In order to measure the expression of TGF-β and VEGF, the cells were cultivated according to the same process as that of Experimental Example 1, and the expression was measured according to the same process as that of Experimental Example 4.

In order to measure the production of melanin, the cells were cultivated and harvested according to the same process as that of Experimental Example 6, and the production of melanin was measured according to the same process as that of Experimental Example 8.

Figure 11:
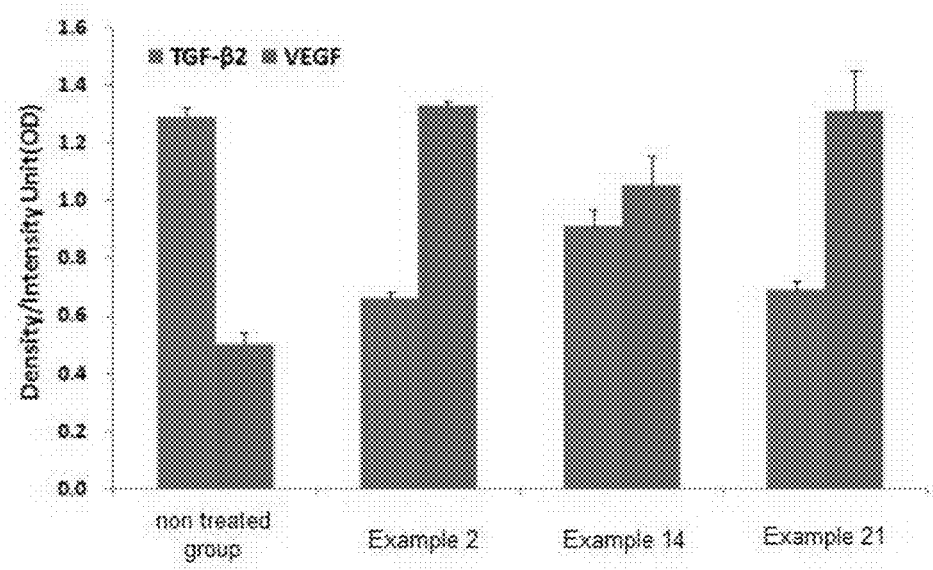
FIG. 11 is a graph showing the expression of TGF-β2 and VEGF in human and mouse melanoma cell lines treated with combination of lanthanum and *capsicum* tincture.
Figure 12:
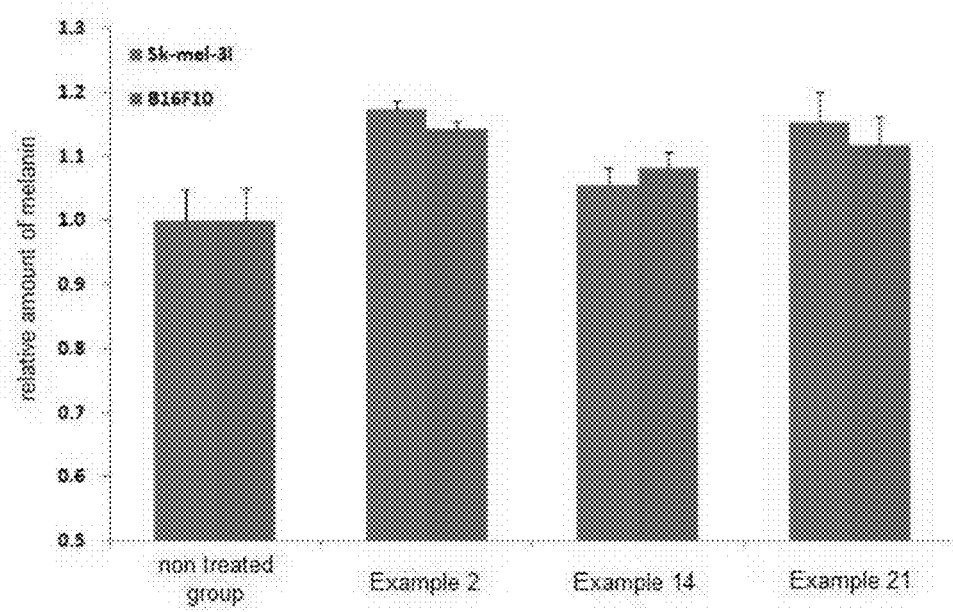
FIG. 12 is a graph showing the melanin production in human and mouse melanoma cell lines treated with combination of lanthanum and *capsicum* tincture.

The results are shown in FIGS. 11 and 12. As shown in FIG. 11, in case of TGF-β, the group treated with the composition of Example 20 containing the combination of lanthanum and *capsicum* tincture showed the similarly decreased expression to the group treated with the composition of Example 2 containing cerium. In case of VEGF, the group treated with the composition of Example 20 containing the combination of lanthanum and *capsicum* tincture showed the similarly increased expression to the group treated with the composition of Example 2 containing cerium. In addition, as shown in FIG. 12, the group treated with the composition of Example 20 containing the combination of lanthanum and *capsicum* tincture showed the similarly increased melanin production to the group treated with the composition of Example 2 containing cerium. The groups treated with the compositions of Examples 21 to 24 containing the combinations of neodymium (Nd), samarium (Sm), gadolinium (Gd) and lutetium (Lu) with *capsicum* tincture, respectively, showed substantially the same effects as the above-described ones.

INDUSTRIAL APPLICABILITY

As described above, the hair improvement composition of the present invention decreases the expression of TGF-β2 to prevent apoptosis of hair follicle cells and promotes the expression of VEGF to increase blood flow from vasodilatory action and to supply nutrients to hair root, thereby to promote hair growth. Thus, the composition of the present invention prevents hair loss, promotes hair regrowth and hair growth, and removes and prevents dandruff. Further, the composition of the present invention activates melanocytes around hair root to increase production of melanin, thereby promoting the formation of black hairs. The composition of the present invention is harmless and safe, has a high absorbability to skin and is not sticky to have good skin feeling, and has no side effect on scalp.

The invention claimed is:

1. A method for slowing hair loss, promoting hair regrowth and hair growth, or promoting black hair formation, comprising the steps:
   1) preparing a composition containing, as an active ingredient, 0.0001 to 10 wt % of a rare earth element selected from the group consisting of cerium (Ce), praseodymium (Pr), promethium (Pm), europium (Eu), terbium (Tb), dysprosium (Dy), holmium (Ho), erbium (Er), thulium (Tm), ytterbium (Yb), scandium (Sc), yttrium (Y), lanthanum (La), neodymium (Nd), samarium (Sm), gadolinium (Gd), lutetium (Lu) and mixtures thereof, and at least one component selected from the group consisting of *capsicum* tincture, tocopherols, salicylic acid, and 1-menthol; and
   2) administering the composition to a subject in need of slowing hair loss, promoting hair regrowth and hair growth, or promoting black hair formation.

2. The method of claim 1, comprising the step of applying cerium (Ce), to the subject.

3. The method of claim 1, comprising the step of applying to the subject the combination of a rare earth element selected from the group consisting of lanthanum (La), neodymium (Nd), samarium (Sm), gadolinium (Gd), lutetium (Lu) and mixtures thereof, with *capsicum* tincture.

4. The method of claim 3, wherein the combination further comprises one or more of ginger tincture and cantharis tincture.

* * * * *